United States Patent [19]
Mitchell et al.

[11] Patent Number: 5,919,979
[45] Date of Patent: Jul. 6, 1999

[54] PREPARATION OF ALKYL FORMAMIDES

[75] Inventors: John William Mitchell, Wescosville; Thomas Albert Johnson, Orefield, both of Pa.

[73] Assignee: Air Products and Chemicals, Inc., Allentown, Pa.

[21] Appl. No.: 08/127,854

[22] Filed: Sep. 28, 1993

[51] Int. Cl.$^6$ .................................................. C07C 231/10
[52] U.S. Cl. ........................... 564/132; 564/123; 564/215
[58] Field of Search ..................................... 564/132, 123, 564/215

[56] References Cited

U.S. PATENT DOCUMENTS

| | | | |
|---|---|---|---|
| 4,098,820 | 7/1978 | Couteau et al. | 260/561 R |
| 4,101,577 | 7/1978 | Smathers | 260/561 R |
| 4,761,499 | 8/1988 | Epstein | 564/132 |

FOREIGN PATENT DOCUMENTS

| | | | |
|---|---|---|---|
| 62-255456 | 11/1987 | Japan | 564/132 |
| 1213173 | 11/1970 | United Kingdom . | |

*Primary Examiner*—Shailendra Kumar
*Attorney, Agent, or Firm*—Mary E. Bongiorno; Russell L. Brewer

[57] ABSTRACT

This invention relates to an improvement in a process for the production of an alkyl formamide, wherein a gas-containing carbon monoxide is reacted at elevated temperature and pressure in reaction zone with a nitrogen-containing compound selected from the group consisting of ammonia, a primary or secondary alkylamine, in the presence of a solvent and a catalyst. The improvement comprises utilizing a solvent comprising a polyethylene glycol, polypropylene glycol, polyethylenepropylene glycol, or mixtures, and an alkali metal or alkaline earth metal alkoxide of a polyethylene glycol, polypropylene glycol, polyethylenepropylene glycol or mixtures as the catalyst.

9 Claims, No Drawings

PREPARATION OF ALKYL FORMAMIDES

TECHNICAL FIELD

This invention pertains to the production of alkyl formamides, particularly dimethylformamide, by the reaction of carbon monoxide with an amine type compound.

DESCRIPTION OF THE PRIOR ART

Several processes for the production of dimethylformamide (DMF) are well known. These are divided into two general categories; one step methods that are carried out via a direct catalytic carbonylation of dimethylamine (DMA), and two step processes in which methyl formate, generally prepared separately in a catalytic reaction of methanol and carbon monoxide is reacted with dimethylamine. Examples of these processes are shown in the following patents:

U.S. Pat. No. 4,101,577 discloses a heterogeneous catalytic process for the production of formamides by contacting an intimate mixture of carbon monoxide, a non-tertiary amine, and a lower alkanol over a strongly basic anion exchange resin. Methanol is preferred because of its volatility and ease of separation from the product.

U.S. Pat. No. 4,098,820 and GB Patent 1,213,173 describe homogeneous catalytic processes. The '820 patent discloses the reaction of carbon monoxide (CO) with a nitrogen containing compound in the presence of a methanolic solution of an alkali metal or alkaline earth metal methoxide catalyst. The '173 patent discloses a process similar to that of '820 except that a pump is used to introduce carbon monoxide gas bubbles into a liquid. The processes differ primarily in the method used to provide CO mixing into the reaction liquid. The '820 patent describes a Buss loop type reactor.

Commercial DMF processes typically employ methanolic solutions of sodium methoxide as catalyst. The co-solvent, methanol, is required to keep sodium methoxide and byproducts, formate and carbonate salts, in solution in the reactor. Crude DMF that exits the reactor is separated from the salts and catalyst (heavies) and from methanol and lights by a series of distillations. In the first distillation, DMF, methanol, and unreacted DMA are stripped away from the salts, sodium methoxide (the catalyst), sodium formate and sodium carbonate (the latter two produced from water and carbon dioxide in the feed). The thick slurry of heavies (salts) in DMF from this distillation is typically treated with water that converts residual catalyst and some DMF to sodium formate, DMA, and methanol. This stream represents a significant yield loss of DMF and sodium methoxide catalyst. Catalyst recovery and recycle in existing processes also are difficult because the catalyst is separated from its solvent during the purification process, and is concentrated with the solid byproducts. An additional concern in existing processes is that the solid byproducts formed (principally sodium formate) tend to precipitate and foul the cooling surfaces in the synthesis reactor.

SUMMARY OF THE INVENTION

This invention relates to an improvement in a process for the production of an alkyl formamide, wherein a gas-containing carbon monoxide is reacted at elevated temperature and pressure in a reaction zone with a nitrogen-containing compound selected from the group consisting of ammonia, a primary or secondary alkylamine, in the presence of a solvent and a catalyst. The improvement comprises utilizing a solvent comprising a polyethylene glycol, polypropylene glycol or polyethylenepropylene glycol and an alkali metal or alkaline earth metal alkoxide of a polyethylene glycol, polyethylenepropylene glycol or polypropylene glycol as the catalyst.

The invention has significant advantages and these include the following:

an ability to eliminate the need of an additional distillation step to remove the co-solvent as is required in prior art methanol processes;

an ability to recover catalyst without substantial losses;

an ability to configure the co-solvent system to allow for effective recycle of the catalyst; and an ability to improve production by reducing the rate of salt plating on heat transfer surfaces thereby resulting in fewer shutdowns.

DETAILED DESCRIPTION OF THE INVENTION

In the production of alkyl formamides, a carbon monoxide containing gas is reacted with a nitrogen-containing compound selected from ammonia, a primary alkyl amine or a secondary alkyl amine in the presence of a catalyst. Examples of nitrogen-containing compounds which are particularly suited for the synthesis of alkyl formamides include ammonia; primary and secondary amines, including $C_{1-8}$ alkylamines and alkanolamines such as methylamine, dimethylamine, ethylamine, diethylamine, propylamine, dipropylamine, butylamine, hexylamine, ethanolamine, diethanolamine, propanolamine, dipropanolamine, etc.; cyclic amines such as cyclohexylamine, cycloheptylamine, benzylamine, aniline, phenylenediamine, phenylethylamine, phenylbutylamine, and heterocyclic amines such as morpholine and piperidine. Of these amines, dimethylamine is the commercial favorite, since it is used to produce the commodity chemical, dimethylformamide.

The catalyst used in effecting carbonylation of the nitrogen-containing compound is an alkali or an alkaline earth metal alkoxide of a polyethylene or polypropylene glycol. As noted in the prior art processes, one of the problems associated with methanol as a substrate for the catalyst and as a solvent for the reaction is that the catalyst itself had poor solubility in the formamides formed by the reaction. These solid precipitates give rise to the clogging of pipes, valves and fouling of heat transfer surfaces.

The utilization of a polyethylene or a polypropylene glycol as a solvent for the catalyst and reaction solves enumerable problems associated with the production of the alkyl formamides. Polyglycols, because of their higher molecular weight and lower volatility, as compared to methanol, provide a mechanism for retaining the catalyst in the reaction mixture comprising the solvent. Methanol, having a higher volatility than the polyethylene and polypropylene glycol is volatilized during the distillation and recovery steps, thereby causing a separation from the catalyst. A second advantage with respect to the use of polyethylene and polypropylene glycols is that the catalyst has greater solubility in the solvent and in mixtures of it with the alkyl formamide present in the reaction medium. Specific examples of suitable polyethylene and polypropylene glycols include the $C_{2-9}$ ethylene glycols and particularly the di, tri, tetra and pentaethylene glycols as well as the di, tri, tetra and pentapropylene glycols or mixtures of the two e.g., ethylene/propylene glycols. A preferred glycol is tetraethylene glycol.

The catalyst is used in the form of a solution in the solvent polyethylene or polypropylene glycol at concentrations ranging from about 1 to 5% by weight of alkali or alkaline earth metal and preferably 2 to 3% by weight. The amount of catalyst added in grams metal per one hundred grams amine will range from about 0.1 to 2, preferably from about 0.4 to 1. Of the alkaline metal and alkaline earth metals, sodium is the preferred metal candidate for preparing the catalyst.

Conditions suited for effecting carbonylation of the nitrogen-containing compounds, particularly mono- and dimethylamine, are substantially similar to those utilized in prior art processes. For example, the molar ratio of carbon monoxide to the nitrogen-containing compound will range from 0.2 to 2 moles and preferably from 0.8 to 1 mole carbon monoxide per mole of nitrogen-containing compound. As is known, if the formate is desired in addition to the formamide, excess carbon monoxide can be incorporated into the reaction for the purpose of enhancing the formate content of the reaction product.

Temperatures and pressure suited for the carbonylation of the nitrogen-containing compound generally will range from 40 to 150° C., preferably 60 to 100° C., and pressures will range from 60 to 3000 psig, preferably 100 to 300 psig. The catalyst utilized in the process is an alkali metal or alkaline earth metal alkoxide of the solvents named, e.g., an alkali metal, e.g., sodium, potassium or an alkaline earth metal alkoxide of the polyethylene or polypropylene glycols, e.g., calcium or magnesium.

The following examples are provided to illustrate various embodiments of the invention and not intended to restrict the scope thereof.

EXAMPLE 1

Diethyleneglycol as Solvent a) Catalyst Preparation

All materials used should be as dry as possible as any moisture in the reaction mixture will deactivate the catalyst.

In a 500 ml multineck stirred flask, 7.2 g of sodium hydride is added to 271.8 g of diethylene glycol over an eight hour period. The vapor space of the flask is continuously swept by nitrogen to avoid moisture absorption that would deactivate the catalyst by forming a precipitate of sodium hydroxide. The flask contents are stirred and degassed overnight to ensure complete reaction of the sodium. The catalyst solution is then removed from the flask, and stored for use in the synthesis reaction.

b) Dimethylformamide Production 471.5 g of DMF is charged to a 1 liter autoclave. Next, 210 cc of DMA is added to the reactor, the contents are stirred, and some of the mixture is removed until the fluid volume in the reactor reaches 495 cc. The reactor contents are heated until the fluid temperature reaches 60° C., at which time the reactor is pressurized with CO to 150 psig. The reactor agitator is turned off while 3 cc of the catalyst solution is added to the reactor via a syringe pump. The reactor agitator is then turned on to 900 RPM, at which point the carbonylation reaction commences. The reactor pressure is maintained at 150 psig by means of CO makeup, at a rate set by a pressure controller. After 90 seconds the agitator is turned off and the reaction ceases. The rate of DMF formation during this period is 0.11 kg/hr per liter of reactor volume. Another 2 cc of catalyst solution is added to the reactor, the agitator is turned on to 900 RPM, and the reaction is allowed to proceed for 60 seconds. The rate during this period is 0.14 Kg/hr. This process of incremental catalyst addition is continued until the rate levels off at approximately 0.45 kg/hr at 21 cc of added catalyst solution.

EXAMPLE 2

Diethyleneglycol as Solvent 470.8 g of DMF is charged to a 1 liter autoclave. Next, 210 cc of DMA is added to the reactor, the contents are stirred, and some of the mixture is removed until the fluid volume in the reactor reaches 495 cc. The reactor contents are heated until the fluid temperature reaches 60° C., at which time the reactor is pressurized with CO to 300 psig. The reactor agitator is turned off while 3 cc of the catalyst solution described in Example 1 is added to the reactor via a syringe pump. The reactor agitator is then turned on to 900 RPM, at which point the carbonylation reaction commences. The reactor pressure is maintained at 300 psig by means of CO makeup, at a rate set by a pressure controller. After 60 seconds the agitator is turned off and the reaction ceases. The rate of DMF formation during this period is 0.39 kg/hr per liter of reactor volume. Another 2 cc of catalyst solution is added to the reactor, the agitator is turned on to 900 RPM, and the reaction is allowed to proceed for 45 seconds. The rate during this period is 0.53 Kg/hr. This process of incremental catalyst addition is continued until the rate levels off at approximately 1.36 kg/hr at 42 cc of added catalyst solution.

EXAMPLE 3

Tetraethyleneglycol as Solvent a) Catalyst Preparation

In a 500 ml multineck stirred flask, 4.7 g of sodium hydride is added to 205.5 g of tetraethylene glycol over an eight hour period. The vapor space of the flask is continuously swept by nitrogen to avoid moisture absorption that would deactivate the catalyst by forming a precipitate of sodium hydroxide. The flask contents are stirred and degassed overnight to ensure complete reaction of the sodium. The catalyst solution is then removed from the flask, and stored for use in the synthesis reaction.

b) Dimethylformamide Production 469.6 g of DMF is charged to a 1 liter autoclave. Next, 210 cc of DMA is added to the reactor, the contents are stirred, and some of the mixture is removed until the fluid volume in the reactor reaches 495 cc. The reactor contents are heated until the fluid temperature reaches 60° C., at which time the reactor is pressurized with CO to 150 psig. The reactor agitator is turned off while 4 cc of the catalyst solution is added to the reactor via a syringe pump. The reactor agitator is then turned on to 900 RPM, at which point the carbonylation reaction commences. The reactor pressure is maintained at 150 psig by means of CO makeup, at a rate set by a pressure controller. After 60 seconds the agitator is turned off and the reaction ceases. The rate of DMF formation during this period is 0.73 kg/hr per liter of reactor volume. Another 4 cc of catalyst solution is added to the reactor, the agitator is turned on to 900 RPM, and the reaction is allowed to proceed for 20 seconds. The rate during this period is 1.56 Kg/hr. This process of incremental catalyst addition is continued until the rate levels off at approximately 3.8 kg/hr at 35 cc of added catalyst solution.

EXAMPLE 4

Tetraethyleneglycol as Solvent 471.6 g of DMF is charged to a 1 liter autoclave. Next, 210 cc of DMA is added to the reactor, the contents are stirred, and some of the mixture is removed until the fluid volume in the reactor reaches 495 cc. The reactor contents are heated until the fluid temperature reaches 60° C., at which time the reactor is pressurized with CO to 300 psig. The reactor agitator is turned off while 3 cc of the catalyst solution described in Example 3 is added to the reactor via a syringe pump. The reactor agitator is then turned on to 900 RPM, at which point the carbonylation reaction commences. The reactor pressure is maintained at 300 psig by means of CO makeup, at a rate set by a pressure controller. After 13 seconds the agitator is turned off and the reaction ceases. The rate of DMF formation during this period is 2.24 kg/hr per liter of reactor volume. Another 3 cc of catalyst solution is added to the reactor, the agitator is turned on to 900 RPM, and the reaction is allowed to proceed for 10 seconds. The rate during this period is 4.68 Kg/hr. This process of incremental catalyst addition is continued until the rate levels off at approximately 8.3 kg/hr at 21 cc of added catalyst solution. Productivities for these tetraethylene glycol based catalyst/solvent systems are significantly greater than those in the prior art processes.

EXAMPLE 5

Catalyst Recycle Using Tetraethyleneglyclol as Solvent

The reactor contents from Example 3 are discharged into a 1000 ml multineck flask. The flask contents are mildly heated under a vacuum pressure of 20 mbar, and the overhead vapors are passed through a water cooled condenser to reflux liquid and to collect product. During a six hour period, overhead product is collected as the flask temperature rises to approximately 50° C. The collected product is found to be 99.6% DMF by weight. The fluid remaining in the flask is collected for use as recycled catalyst.

470.2 g of DMF is charged to a 1 liter autoclave. Next, 210 cc of DMA is added to the reactor, the contents are stirred, and some of the mixture is removed until the fluid volume in the reactor reaches 495 cc. The reactor contents are heated until the fluid temperature reaches 60° C., at which time the reactor is pressurized with CO to 150 psig. The reactor agitator is turned off while 4 cc of the catalyst solution recovered from the distillation described above is added to the reactor via a syringe pump. The reactor agitator is then turned on to 900 RPM, at which point the carbonylation reaction commences. The reactor pressure is maintained at 150 psig by means of CO makeup, at a rate set by a pressure controller. After 60 seconds the agitator is turned off and the reaction ceases. The rate of DMF formation during this period is 0.30 kg/hr per liter of reactor volume. Another 4 cc of catalyst solution is added to the reactor, the agitator is turned on to 900 RPM, and the reaction is allowed to proceed for 30 seconds. The rate during this period is 1.34 Kg/hr. This process of incremental catalyst addition is continued until the rate levels off at approximately 3.2 kg/hr at 21 cc of added catalyst solution. This level of productivity is approximately 84% of that reported in Example 3 that used a fresh tetraethylene glycol based catalyst solution at similar conditions of temperature and pressure.

This example shows that catalyst recycle using the tetraethylene glycol solvent is both straight forward and effective. Catalyst recycle in the prior art processes is difficult because the catalyst is separated from its low boiling methanol solvent in the product purification, and is concentrated with the solid byproducts.

EXAMPLE 6

Comparison to Existing Technologies

The performance parameters using a polyethylene glycol are compared to prior art processes in Table 1.

TABLE 1

| Run | Catalyst loading, g Na/100 g DMA | Temp. ° C. | Pressure psig | DMF Productivity Kg/hr/liter | Catalyst efficiency, g DMF/ g Na |
|---|---|---|---|---|---|
| Example 1 | 0.47 | 60 | 150 | .45 | 345 |
| Example 2 | 0.94 | 60 | 300 | 1.36 | 173 |
| Example 3 | 0.68 | 60 | 150 | 3.8 | 239 |
| Example 4 | 0.41 | 60 | 300 | 8.3 | 398 |
| Example 5 | 0.68 | 60 | 150 | 3.2 | 398 |
| Prior Art | | | | | |
| Example 1 of U.S. Pat. No. 4,098,820 | 0.34 | 90 | 304 | 2.1 | 475 |
| Example 6 of GB 1,213,173 | 0.27 | 120 | 275 | .43 | 591 |
| Example of U.S. Pat. No. 2,866,822 | 0.51 | 70 | 50 | .70 | 315 |

It is clear from Table 1 that, relative to the prior art processes (which all use methanol as a catalyst co-solvent), the use of polyethylene glycols yields excellent DMF productivity, even at mild conditions of temperature. The diethylene glycol based catalysts of Examples 1 and 2 have DMF productivities that are comparable to the prior art. The tetraethylene glycol based catalysts of Examples 3–5 have significantly higher productivities. The Example 4 catalyst shows nearly a fourfold increase in DMF productivity over that disclosed in the prior art process described in the '820 patent even though the temperature employed is 30° C. lower. Single pass catalyst efficiency for the glycol based catalysts is comparable to that reported in the prior art processes. When catalyst recycle is considered, the catalyst efficiency can be enhanced significantly. Since the Example 5 catalyst is a recycle from the Example 3 catalyst, the total efficiency of this catalyst is 637 g DMF/g Na which is greater than that reported in the prior art. Since the catalyst is not separated from its solvent in the current invention, multiple recycles of the catalyst are possible. This will result in overall catalyst efficiencies which greatly exceed those in the prior art, where catalyst recycle is not feasible.

We claim:

1. In a process for the production of an alkyl formamide, wherein a gas-containing carbon monoxide is reacted at elevated temperature and pressure in a reaction zone with a nitrogen-containing compounds selected from the group consisting of ammonia, a primary alkylamine and a secondary alkylamine, in the presence of a solvent and a catalyst, the improvement which comprises:

utilizing a polyethylene glycol as a solvent and utilizing an alkali metal or alkaline earth metal alkoxide of a polyethylene glycol, polypropylene glycol, polyethylenepropylene glycol or mixtures thereof as the catalyst.

2. The process of claim 1 wherein the nitrogen-containing compound is a primary or secondary alkylamine, wherein each alkyl group of the alkylamine has from 1 to 6 carbon atoms.

3. The process of claim 2 wherein the solvent is selected from the group consisting of di, tri, and tetraethyleneglycol.

4. The process of claim 3 wherein the alkali metal or alkaline earth metal in said catalyst is selected from the group consisting of sodium, lithium, calcium and magnesium.

5. The process of claim 4 wherein the alkali metal is sodium.

6. The process of claim 5 wherein the catalyst is present in an amount from 1 to 5 percent by weight of the solvent.

7. The process of claim 6 wherein the amine is monomethylamine or dimethylamine.

8. The process of claim 7 wherein the glycol is tetraethyleneglycol.

9. The process of claim 7 wherein the catalyst is added to provide from 0.1 to 2 grams metal per 100 grams amine.

* * * * *